US00PP28905P3

(12) United States Plant Patent
Magee

(10) Patent No.: US PP28,905 P3
(45) Date of Patent: Jan. 30, 2018

(54) *ILEX* PLANT NAMED 'EN2'

(50) Latin Name: *Ilex×hybrida*
Varietal Denomination: EN2

(71) Applicant: Jack Mitchell Magee, Poplarville, MS (US)

(72) Inventor: Jack Mitchell Magee, Poplarville, MS (US)

( * ) Notice: Subject to any disclaimer, the term of this patent is extended or adjusted under 35 U.S.C. 154(b) by 17 days.

(21) Appl. No.: 14/998,741

(22) Filed: Feb. 9, 2016

(65) Prior Publication Data

US 2017/0231139 P1 Aug. 10, 2017

(51) Int. Cl.
*A01H 5/12* (2006.01)

(52) U.S. Cl.
USPC ..... Plt./247

(58) Field of Classification Search
USPC ..... Plt./247
See application file for complete search history.

*Primary Examiner* — Keith O Robinson
(74) *Attorney, Agent, or Firm* — C. A. Whealy

(57) ABSTRACT

A new and distinct *Ilex* plant named 'EN2', characterized by its uniform and mounding plant habit; freely branching habit; dense and bushy growth habit; glossy medium green-colored leaves; and good garden performance.

2 Drawing Sheets

Botanical designation: *Ilex×hybrida*.
Cultivar denomination: 'EN2'.

CROSS-REFERENCED TO CLOSELY-RELATED APPLICATIONS

Title: *Ilex* Plant Named 'EN1'
Applicant: Jack Mitchell Magee
Filed: Feb. 9, 2016
Application Ser. No.: 14/998,742

BACKGROUND OF THE INVENTION

The present Invention relates to a new and distinct *Ilex* plant, botanically known as *Ilex×hybrida* and hereinafter referred to by the name 'EN2'.

The new *Ilex* plant is a product of a planned breeding program conducted by the Inventor in Poplarville, Miss. The objective of the breeding program was to develop new large, dense and uniform *Ilex* plants with mounding or pyramidal plant form and dark green-colored leaves.

The new *Ilex* plant originated from a cross-pollination during the spring of 2003 of an unidentified proprietary selection of *Ilex×hybrida*, not patented, as the female, or seed, parent with *Ilex×hybrida* 'Conaf', disclosed in U.S. Plant Pat. No. 9,487, as the male, or pollen, parent. The new *Ilex* plant was discovered and selected by the Inventor in 2005 as a single plant within the progeny of the stated cross-pollination in a controlled environment in Poplarville, Miss.

Asexual reproduction of the new *Ilex* plant by softwood cuttings in Poplarville, Miss. since 2006 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'EN2'. These characteristics in combination distinguish 'EN2' as a new and distinct *Ilex* plant:

1. Uniform and mounding plant habit.
2. Freely branching habit; dense and bushy growth habit.
3. Glossy medium green-colored leaves.
4. Good garden performance.

Plants of the new *Ilex* differ from plants of the female parent selection in the following characteristics:

1. Plants of the new *Ilex* are more uniform and denser than plants of the female parent selection.
2. Plants of the new *Ilex* have better leaf retention than plants of the female parent selection.
3. Leaves of plants of the new *Ilex* are glossier and darker green in color than leaves of plants of the female parent selection.

Plants of the new *Ilex* differ from plants of the male parent, 'Conaf', in the following characteristics:

1. Plants of the new *Ilex* are more compact and mounding than plants of 'Conaf'.
2. Plants of the new *Ilex* have smaller leaves than plants of 'Conaf'.

Plants of the new *Ilex* can be compared to plants of *Ilex×hybrida* 'EN1', disclosed in U.S. Plant patent application Ser. No. 14/998,742. Plants of the new *Ilex* differ from plants of 'EN1', in the following characteristics:

1. Plants of the new *Ilex* are taller than plants of 'EN1'.
2. Plants of the new *Ilex* are more vigorous than plants of 'EN1'.
3. Plants of the new *Ilex* are more freely branching than plants of 'EN1'.

Plants of the new *Ilex* can be compared to the plants of *Ilex×meservaea* 'Blue Princess', not patented. In side-by-side comparisons conducted in Poplarville, Miss., plants of the new *Ilex* differed from plants of 'Blue Princess' in the following characteristics:

1. Plants of the new *Ilex* were more compact, mounding and uniform than plants of 'Blue Princess'.
2. Plants of the new *Ilex* had larger leaves than plants of 'Blue Princess'.
3. Plants of the new *Ilex* and 'Blue Princess' differed in fruit color as plants of 'Blue Princess' had darker red-colored fruits.

Plants of the new *Ilex* can be compared to the plants of *Ilex×meservaea* 'Mesog', disclosed in U.S. Plant Pat. No. 4,878. In side-by-side comparisons conducted in Poplarville, Miss., plants of the new *Ilex* differed from plants of 'Mesog' in the following characteristics:

1. Plants of the new *Ilex* had larger leaves than plants of 'Mesog'.
2. Plants of the new *Ilex* and 'Mesog' differed in fruit color as plants of 'Mesog' had darker red-colored fruits.

Plants of the new *Ilex* can also be compared to the plants of *Ilex×meserveae* 'Magland', disclosed in U.S. Plant Pat. No. 4,878. In side-by-side comparisons conducted in Poplarville, Miss., plants of the new *Ilex* differed from plants of 'Magland' in the following characteristics:

1. Plants of the new *Ilex* were more mounding than and not as upright and pyramidal as plants of 'Magland'.
2. Plants of the new *Ilex* were smaller than and not as apically dominant as plants of 'Magland'.
3. Plants of the new *Ilex* had glossier leaves than plants of 'Magland'.
4. Plants of the new *Ilex* were more freely flowering and fruiting than plants of 'Magland'.
5. Plants of the new *Ilex* and 'Magland' differed in fruit color as plants of 'Magland' had lighter red-colored fruits.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of typical plants of 'EN2'.

The photograph on the second sheet is a close-up view of a stem of 'EN2' with leaves and developing and developed fruits.

DETAILED BOTANICAL DESCRIPTION

The aforementioned photographs and following observations and measurements describe plants grown during the autumn in #7 containers in a polypropylene-covered shadehouse in Park Hill, Okla. and under cultural practices typical of commercial *Ilex* production. During the production of the plants, day temperatures averaged 23° C. and night temperatures averaged 9° C. Plants were eight years old when the photographs and detailed description were taken. In the following description, color references are made to The Royal Horticultural Society Colour Chart, 2001 Edition, except where general terms of ordinary dictionary significance are used.

Botanical classification: *Ilex×hybrida* 'EN2'.

Parentage:

*Female, or seed, parent.*—Unidentified proprietary selection of *Ilex×hybrida,* not patented.

*Male, or pollen, parent.*—*Ilex×hybrida* 'Conaf', disclosed in U.S. Plant Pat. No. 9,487.

Propagation:

*Type.*—By softwood cuttings.

*Time to initiate roots, summer.*—About three weeks at temperatures about 32° C.

*Time to initiate roots, winter.*—About six weeks at temperatures about 5.5° C.

*Time to produce a rooted young plant, summer.*—About four months at temperatures about 32° C.

*Time to produce a rooted young plant, winter.*—About six months at temperatures about 5.5° C.

*Root description.*—Medium in thickness, fleshy; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Perennial shrub; uniform and mounding plant habit; vigorous growth habit.

*Branching habit.*—Freely branching habit; dense and bushy growth habit with about 35 lateral branches developing per plant.

*Plant height.*—About 3 meters to 3.6 meters.

*Plant diameter, area of spread.*—About 2.4 meters to 3 meters.

*Lateral branch description.*—Length: About 45.75 cm. Diameter: About 1.3 cm to 3.8 cm. Internode length: About 2 cm. Strength: Strong; stiff, not flexible. Texture: Smooth, glabrous. Color: Close to 144A.

*Leaf buds.*—Length: About 1.5 mm. Diameter: About 2 mm. Texture: Smooth, glabrous. Color: Close to 59B.

*Leaf description.*—Arrangement: Alternate, simple. Length: About 6.5 cm. Width: About 3.4 cm. Shape: Ovate to lanceolate. Apex: Acuminate. Base: Cuneate. Margin: Entire with spines. Venation pattern: Pinnate. Aspect: Mostly horizontal. Fragrance: None detected. Texture and luster, upper surface: Smooth, glabrous; glossy. Texture and luster, lower surface: Smooth, glabrous; matte. Color: Developing leaves, upper surface: Close to 144A. Developing leaves, lower surface: Close to 143D. Fully expanded leaves, upper surface: Close to N134B; venation, close to 143C. Fully expanded leaves, lower surface: Close to 143A; venation, close to 143C. Petioles: Length: About 8 mm. Diameter: About 2 mm. Aspect: About 30° from stem axis. Texture, upper and lower surfaces: Smooth, glabrous. Color, upper and lower surfaces: Close to 143C.

*Stipules.*—Stipule development has not been observed on plants of the new *Ilex.*

Flower description:

*Flower appearance and arrangement.*—Axillary rotate flowers arranged in clusters; flowers face upright to outwardly; flowers inconspicuous; about 5 to 50 flowers develop per lateral branch.

*Natural flowering season.*—Plants flower during the spring in Oklahoma.

*Flower longevity.*—Flowers last about four days on the plant; flowers not persistent.

*Fragrance*.—None detected.

*Flower diameter*.—About 3.5 mm by 5 mm.

*Flower length* (*height*).—About 3.5 mm.

*Flower buds*.—Length: About 2 mm. Diameter: About 1 mm. Shape: Ovoid. Color: Close to 140B.

*Petals*.—Quantity and arrangement: Four in a single whorl. Length: About 2 mm. Width: About 1.5 mm. Shape: Obovate. Apex: Obtuse. Base: Cuneate. Margin: Entire. Texture, upper and lower surfaces: Smooth, glabrous. Color: When opening, upper and lower surfaces: Close to 155D. Fully opened, upper and lower surfaces: Close to 155D; color does not change with development.

*Sepals*.—Quantity and arrangement: Four in a single whorl; fused at the base, imbricate. Length: About 1 mm. Diameter: About 1.5 mm. Shape: Ovate. Apex: Acute. Base: Truncate, fused. Margin: Entire. Texture, upper and lower surfaces: Smooth, glabrous. Color, upper and lower surfaces: Close to 144C.

*Peduncles*.—Length: About 8 mm. Diameter: Less than 1 mm. Aspect: About 45° from stem axis. Strength: Strong; flexible. Texture: Smooth, glabrous. Color: Close to 144C.

*Reproductive organs*.—Androecium: Quantity per flower: About four. Filament length: About 1 mm. Filament color: Close to 4D. Anther length: About 1 mm. Anther shape: Ovoid. Anther color: Close to 2C. Pollen amount: Moderate. Pollen color: Close to 2D. Gynoecium: Quantity per flower: One. Pistil length: About 1.5 mm. Style color: Close to 140B. Stigma shape: Globular with three lobes. Stigma color: Close to 140B. Ovary color: Close to 140B.

*Fruits*.—Length: About 7 mm. Diameter: About 7 mm. Shape: Ovoid. Texture: Smooth, glabrous. Color: Close to 44B.

*Seeds*.—Quantity per fruit: About four. Length: About 7 mm. Diameter: About 3 mm. Shape: Oblong. Texture: Smooth, glabrous. Color: Close to 152D.

Garden performance: Plants of the new *Ilex* have been observed to have good garden performance and to be tolerant to rain, wind and low temperatures about −23° C.

Pathogen & pest resistance: Plants of the new *Ilex* have been observed to be resistant to root rots, *Phytophthora* and *Pythium*, and to be tolerant to Melon Aphids (*Aphis gossypii*) and Two-spotted Spider Mites (*Tetranychus urticae*).

It is claimed:

1. A new and distinct *Ilex* plant named 'EN2' as illustrated and described.

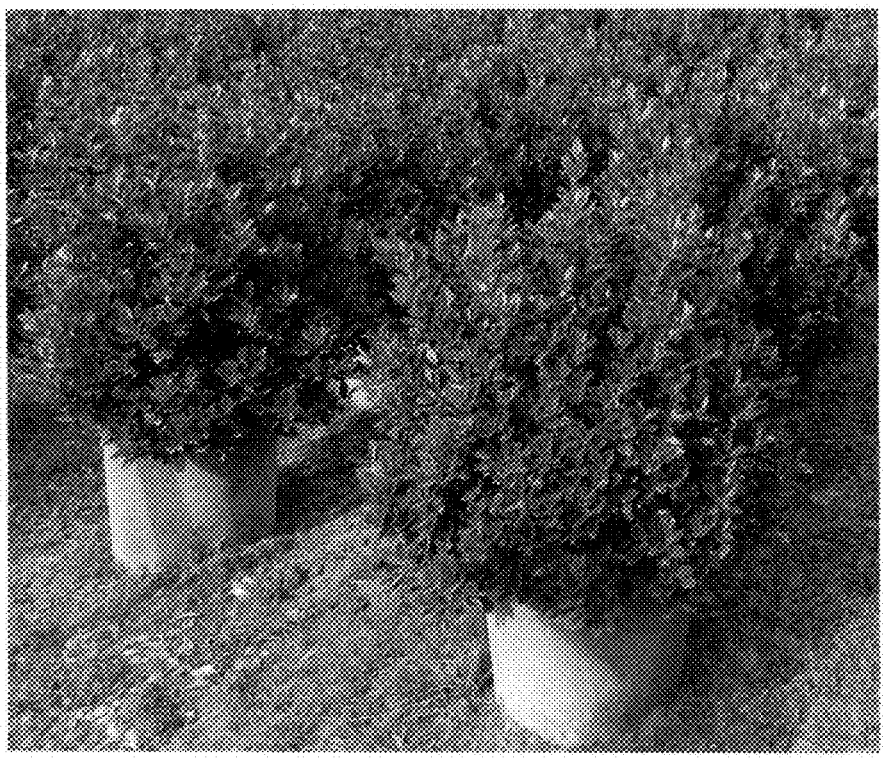

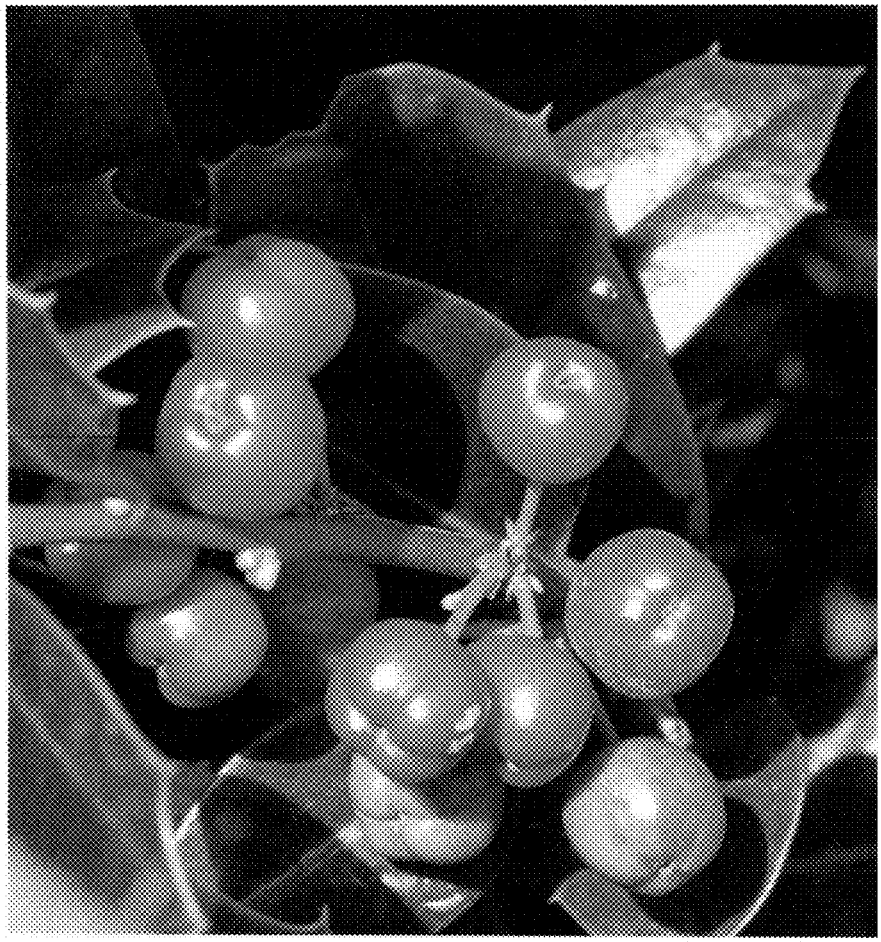

* * * * *